(12) United States Patent
Despres et al.

(10) Patent No.: US 12,091,627 B2
(45) Date of Patent: Sep. 17, 2024

(54) METHOD FOR PRODUCING A BIOFUEL BY STEAM CRACKING

(71) Applicant: EUROPEENNE DE BIOMASSE, Paris (FR)

(72) Inventors: Jean-Luc Despres, Verzenay (FR); Thomas Habas, Paris (FR); Adriana Quintero-Marquez, Le Vesinet (FR); Frédéric Martel, Riems (FR)

(73) Assignee: EUROPEENNE DE BIOMASSE, Paris (FR)

( * ) Notice: Subject to any disclaimer, the term of this patent is extended or adjusted under 35 U.S.C. 154(b) by 114 days.

(21) Appl. No.: 17/597,057

(22) PCT Filed: Jun. 17, 2020

(86) PCT No.: PCT/FR2020/051047
§ 371 (c)(1),
(2) Date: Dec. 23, 2021

(87) PCT Pub. No.: WO2020/260801
PCT Pub. Date: Dec. 30, 2020

(65) Prior Publication Data
US 2022/0315854 A1     Oct. 6, 2022

(30) Foreign Application Priority Data
Jun. 24, 2019  (FR) ..................... 1906800

(51) Int. Cl.
*C10L 9/08* (2006.01)
*C10L 5/36* (2006.01)
*C10L 5/44* (2006.01)

(52) U.S. Cl.
CPC .............. *C10L 9/08* (2013.01); *C10L 5/363* (2013.01); *C10L 5/442* (2013.01); *C10L 5/445* (2013.01);
(Continued)

(58) Field of Classification Search
CPC .......... C10L 5/363; C10L 5/442; C10L 5/445; C10L 9/08; C10L 2200/0469; C10L 2290/148; C10L 2290/58; C10L 2290/60
See application file for complete search history.

(56) References Cited

U.S. PATENT DOCUMENTS

| 8,057,639 B2 | 11/2011 | Pschorn et al. |
| 2013/0341569 A1* | 12/2013 | Ampulski ............... C10L 9/083 422/162 |
| 2018/0334629 A1* | 11/2018 | Scalzo .................... C10L 5/442 |

FOREIGN PATENT DOCUMENTS

| CN | 105806735 A | 7/2016 | |
| EP | 2868731 A1 * | 5/2015 | ............... C10G 9/36 |

(Continued)

OTHER PUBLICATIONS

English-language machine translation of EP 2868731 A1 (Year: 2015).*

(Continued)

*Primary Examiner* — James C Goloboy
(74) *Attorney, Agent, or Firm* — TraskBritt

(57) ABSTRACT

A method for producing a biofuel by continuous or discontinuous steam cracking of lignocellulosic biomass, comprises: —recording a digital model of the optimal steam cracking parameters as a function of the typology of the plant constituents of the biomass; —supplying the steam cracking reactor with heterogeneous biomass; —measuring at least once during the treatment the typology of the plant constituents of the biomass; and —controlling the adjustment of the steam cracking parameters as a function of the typology of the plant constituents of the measured biomass and of the digital model.

13 Claims, 1 Drawing Sheet

(52) U.S. Cl.
  CPC . *C10L 2200/0469* (2013.01); *C10L 2290/148* (2013.01); *C10L 2290/58* (2013.01); *C10L 2290/60* (2013.01)

(56) References Cited

FOREIGN PATENT DOCUMENTS

| JP | 2012-229326 | A |  | 11/2012 | |
|----|-------------|---|--|---------|--|
| JP | 2015-527425 | A |  | 9/2015 | |
| WO | 2003/071025 | A2 |  | 8/2003 | |
| WO | WO-2012109490 | A2 | * | 8/2012 | ............... C10J 3/66 |
| WO | WO-2018229621 | A1 | * | 12/2018 | ............... C07C 4/04 |

OTHER PUBLICATIONS

B. V. Babu. "Biomass pyrolysis: a state-of-the-art review" Biofuels, Bioproducts & Biorefining, GB, vol. 2, No. 5, Sep. 1, 2008 (Sep. 1, 2008), pp. 393-414.

International Search Report for International Application No. PCT/FR2020/051047, mailed Dec. 9, 2020, 10 pages (4 pages of English Translation and 6 pages of Original Document).

International Written Opinion for International Application No. PCT/FR2020/051047, mailed Dec. 9, 2020 17 pages (8 pages of English Translation and 9 pages of Original Document).

Ramos Ana et al. "Co-gasification and recent developments on waste-to-energy conversion: A review" Renewable and Sustainable Energy Reviews, vol. 81, Aug. 7, 2017 (Aug. 7, 2017), pp. 380-398.

Sagehashi M et al. "Superheated steam pyrolysis of biomass elemental components and Sugi (Japanese cedar) for fuels and chemicals" Bioresource Technology, Elsevier, Amsterdam, NL, vol. 97, No. 11, Jul. 1, 2006 (Jul. 1, 2006), pp. 1272-1283.

Chinese First Office Action for Application No. 202080058011.9 dated Aug. 18, 2023, 8 pages.

Indian Office Action for Application No. 202217003051 dated Sep. 20, 2023, 8 pages.

Japanese Notification of Reasons for Refusal for Application No. 2021-576622 dated Jan. 6, 2024, 6 pages.

* cited by examiner

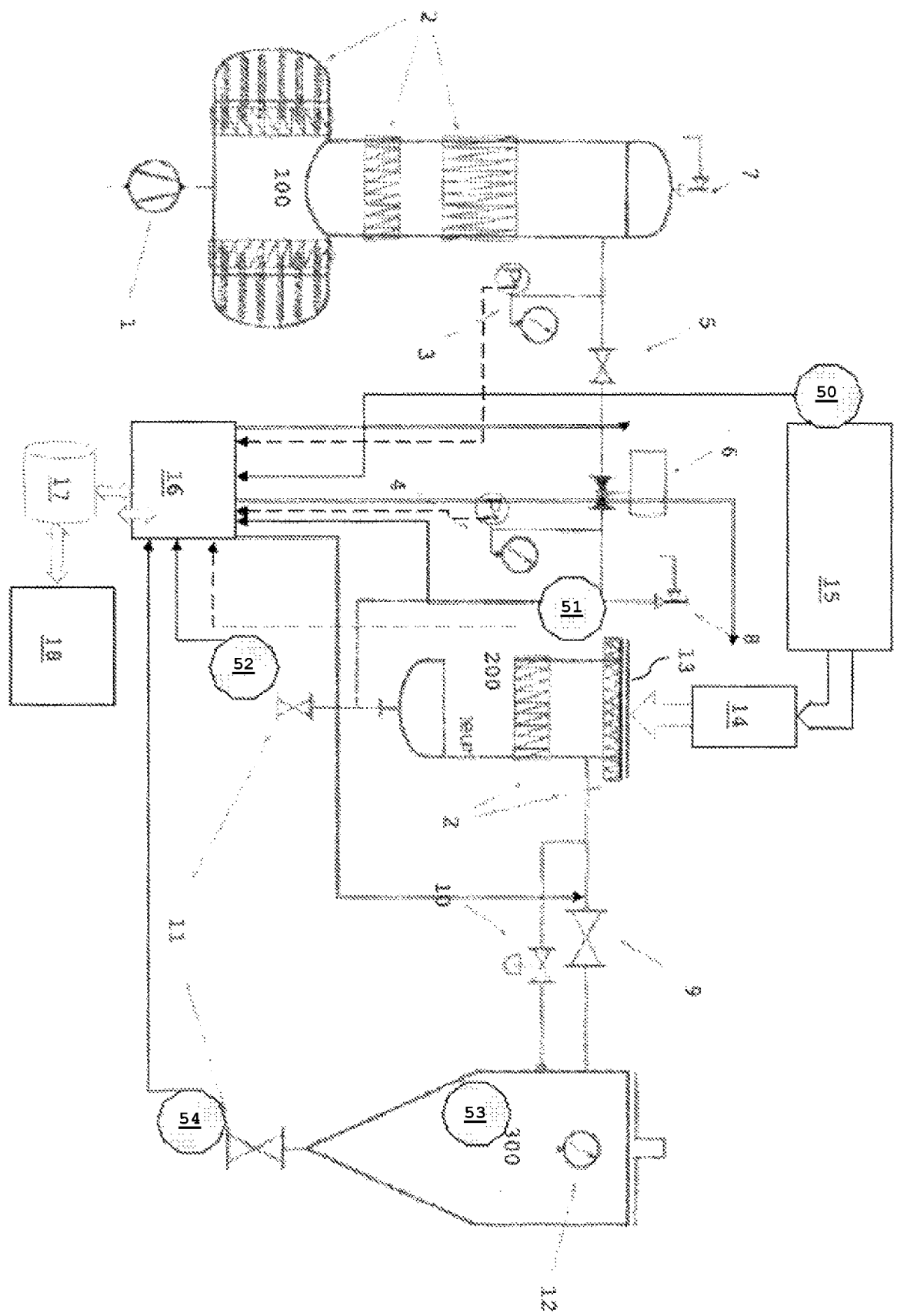

METHOD FOR PRODUCING A BIOFUEL BY STEAM CRACKING

CROSS-REFERENCE TO RELATED APPLICATIONS

This application is a national phase entry under 35 U.S.C. § 371 of International Patent Application PCT/FR2020/051047, filed Jun. 17, 2020, designating the United States of America and published as International Patent Publication WO 2020/260801 A1 on Dec. 30, 2020, which claims the benefit under Article 8 of the Patent Cooperation Treaty to French Patent Application Serial No. 1906800, filed Jun. 24, 2019.

TECHNICAL FIELD

The present disclosure relates to the production of solid biofuels originating from treatment of biomass of various origins, by means of a steam cracking or steam explosion method.

BACKGROUND

Biomass is a renewable primary energy, which can be transported to its transformation site, but is a low-density, variable and perishable source of energy.

The transformation of lignocellulosic biomass (wood, agricultural waste, co-products of agriculture and the agro-industry) into an energy-dense, transportable, and easily storable compound, makes it possible to develop and consolidate a stationary energy industrial sector (biofuel used at a fixed point, at home, in contrast with biofuel oils), and to reduce the environmental impacts ($CO_2$ fossil emission, with a biomass without fertilizers or phytosanitaries).

The heat treatment of the biomass by steam cracking allows for this densification of energy, and modifies the structure of the treated biomass:
   the lignocellulosic materials are defibrillated
   the crystallinity of the cellulose is increased as a result of the crystallization of the amorphous portions
   the hemicelluloses are easily hydrolyzed
   the delignification is promoted as a result of modifications in the structure of the lignin.

The steam explosion is a biomass treatment that is commonly used for the production of biofuels, in particular, in the form of granules ("black pellets"). It simultaneously uses both physical/mechanical methods and chemical methods in order to break the structure of the lignocellulosic material. In general terms, steam explosion is a violent evaporation or flash evaporation of water into steam. The pressurized containers, which operate above atmospheric pressure can also provide the conditions for rapid boiling, which can be characterized as steam explosion. The biomass introduced into a steam cracking reactor, continuously or in batches, is rapidly heated by means of saturated steam under high pressure. The biomass/steam mixture is retained for a period of time, in order to promote the hydrolysis of the hemicelluloses, and other chemical and physical changes. This period is then followed by explosive decompression. The steam explosion is typically initiated at a temperature of 160-260° C. for a few seconds to a few minutes, before the material is exposed to atmospheric pressure.

The apparatus for steam explosion consists in an evaporator (steam generator) and a reactor, which is subjected to rapid decompression. Steam explosion can be described as being made up of two successive phases: steam cracking (i.e., breaking complex molecules into smaller molecules under the effect of steam), and explosive decompression.

The first phase consists in causing steam, under high pressure, to penetrate into the interior of the structure of the material. Thus, the steam condenses and wets the surface of the material. The condensed water initiates the hydrolysis of acetyl and methylglucuronic acid groups present in the hemicelluloses. The acids thus freed reduce the pH of the medium, and catalyze the depolymerization of the hemicelluloses. The application of more drastic conditions allows for the formation of monosaccharides, while increasing the furfural and 5-hydroxymethylfurfural concentration, which are fermentation inhibitors.

During the second phase, the explosive decompression results in the instantaneous evaporation of some of the condensation water present in the structure. This expansion of the water vapor exerts a shearing force on the surrounding structure. If the shearing force is sufficiently high, the steam will cause the mechanical breakage of the lignocellulosic structures. The combined effects of the two stages include the modification of the physical properties of the material (specific surface area, water retention, coloration, crystallinity of the cellulose, etc.), the hydrolysis of the hemicellulosic compounds, and the modification of the chemical structure of the lignin, allowing for the opening of the material, and facilitating the extraction thereof.

The two parameters controlling the steam explosion are the reaction temperature and the residence time. The time that the biomass spends in the reactor helps to determine the degree of hydrolysis of the hemicelluloses by the organic acids. However, long residence times will also increase the production of degradation products, which must be minimized in a following fermentation method. The temperature controls the steam pressure in the reactor. Higher temperatures result in higher pressures, thus increasing the difference between the reactor pressure and the atmospheric pressure. The pressure difference is in turn proportional to the shearing force.

The parameters of the method are critical, and, in order to facilitate the comparison of different options, a model has been developed that is based on the hypotheses that the kinetics of the method is of the first order and obeys the Arrhenius law, making it possible to develop the ordinate of the reaction (R0):

$$R0 = \int \exp[(Tr-Tb)/14.75] \, dt$$

Where Tr is the reaction temperature (° C.), Tb is the baseline temperature (boiling point of water at atmospheric pressure: 100° C.), t is the residence time (min), and 14.75 is the conventional activation energy, supposing that the general method is hydrolytic, and the general conversion is of the first order. The log 10 value of the ordinate of the reaction gives the severity factor (or severity), which is used to represent the effects of the steam explosion on the biomass:

$$\text{Severity} = \log 10(R0)$$

Generally, the production of biofuels by steam cracking is carried out starting from natural biomass, originating from logging or coppicing, or products derived from timber exploitation, or indeed other agricultural products, and the operating point is optimized so as to obtain a good energy quality for the steam-cracked powder.

The steam-cracking differs from hydrothermal pre-treatment, also referred to as aqueous fractionation, solvolysis, hydrothermolysis, or hydrothermal treatment, in that the latter consists in using water at a high temperature and high pressure in order to promote the disintegration and the separation of the lignocellulosic matrix. This technique is not suitable for the production of black pellets, since the products obtained are largely liquid.

The pyrolysis is the chemical decomposition of an organic compound, by intense heating in the absence of oxygen. The compounds obtained following pyrolysis differ, in terms of their characteristics, from those obtained by steam cracking. The steam cracking cannot be likened to a pyrolysis technique, in that it uses steam explosion and is carried out in the presence of oxygen.

Pyrolysis techniques using digital models in order to optimize the parameters of their methods are known, for example, from the document WO2012/109490 or the document CN105806735A. These known pyrolysis techniques are based on the chemical decomposition of an organic compound, by intense heating in the absence of oxygen.

The document BV BABU "Biomass pyrolysis: a State of the art review" also describes prior art of pyrolysis techniques. However, these methods differ from steam cracking techniques.

The American patent US2013/341569 describes methods for pre-treatment of the biomass, comprising a step of steam cracking in order to generate the synthesis gas. This method also comprises a catalytic converter, which uses a control system, which, depending on the composition of the catalyst material, adjusts the gas conversion. In this patent, use is made of a digital model for the step of steam cracking, in order to obtain the optimal parameters, depending on the nature and the content of the contaminants. This document discloses a control method that is involved in the catalytic converter, without making any mention of steam cracking control.

Finally, SAGEHASMI ET AL: "Superheated steam pyrolysis of biomass elemental components and Sugi (Japanese cedar) for fuels and Chemicals" discloses a method using a digital model for superheated steam pyrolysis, the application of which is limited to specimens of some individual constituents of biomass (xylan, cellulose, lignin, etc.), or to a single type of biomass, i.e., the Japanese cedar (Table 1 page 1273; right-hand column, page 1273, lines 1-5).

In the case of the solutions known in the prior art, the best solution for guaranteeing the best result of the steam cracking is to make a regular and controlled supply of biomass of the same quality. In the case of wood, it is a question of providing homogeneous batches of wood of the same species of the same plot of land, with a selection of tree sizes and trunk diameters, in particular, so as to have regular debarking. In the case of variable resources, attempts should be made to group these by homogeneous batches, and to supply the steam cracker with these batches, and to readjust the steam cracking operating parameters upon each change of batch and quality. This requires traceability and compliance with the specifications by the biomass suppliers, a high level of confidence, and, at the factory level, an ability to identify the batch or quality changes in order to modify the conduct of the operations. However, this does not prevent some batches being mixed with other species, variable ages, or different qualities, of biomasses.

The solutions of the prior art are not entirely satisfactory, since they either make use of pyrolysis methods, provide for parameter control merely for a catalytic converter, or indeed require a supply of homogeneous biomass, which can prove to be restrictive.

Indeed, the pyrolysis methods do not make it possible to obtain compounds having characteristics that are satisfactory for producing black pellets.

In the prior art, the use of a digital model is applied only:
to pyrolysis systems that do not make it possible to obtain compounds having the characteristics required for obtaining black pellets
to systems that do not involve steam cracking parameterization in the digital model.

The particle size and the energy efficiency decrease when the severity factor increases.

Vice versa, if the severity factor is insufficient, the calorific value of the steam-cracked material reduces, and the product is more fibrous than pulverulent, which makes it difficult to shape it into pellets.

When the supply of biomass exhibits heterogeneities, the solutions of the prior art require sorting of the supply at different stages—at the logging or harvesting site, during loading, at the wood or biomass storage, during preparation stages (debarking, destoning, grinding). It would thus be necessary to regroup and recreate homogenous batches using the overflow, which results in requirements in handling, storage, traceability, and does not prevent different products from passing through the screen.

BRIEF SUMMARY

In order to overcome the disadvantages of the prior art regarding the lesser availability of uniform and homogeneous natural biomass, and the inadequacy of known facilities for the treatment of heterogeneous biomass, the present disclosure relates, according to the most general meaning thereof, to a method for continuous or discontinuous production of a biofuel by steam cracking of lignocellulosic plant biomass, characterized in that:
a digital model of the optimal steam cracking parameters depending on the typology of the plant constituents of the biomass is recorded
the steam cracking reactor is supplied with heterogeneous biomass
the typology of the plant constituents of the biomass is measured at least once during the treatment
the adjustment of the steam cracking parameters is controlled depending on the typology of the plant constituents of the biomass and on the digital model.

Within the meaning of the present disclosure, "typology of the plant constituents of the biomass" means the combination of different constituents of the biomass (lignin, cellulose, etc.), as well as the relative proportions thereof, which define the nature of the biomass. Each type of biomass has a particular typology due to its constituents, and is moreover defined by indicators. The indicators are, for example, the level of heterogeneity of the biomass, or the nature thereof.

Thus, within the context of the present disclosure, the biomass treated can be made up of a mixture of different types of biomasses having different indicators; reference is thus made to "heterogeneous biomass."

According to an advantageous embodiment, the lignocellulosic biomass has a humidity of less than 27%, and directly undergoes a steam cracking treatment without any other preceding heat or chemical treatment.

According to variants:
the adjusted parameter comprises at least one of the following parameters: severity factor, steam cracking pressure, steam cracking temperature, steam cracking duration, cessation of steam cracking, steam/solid ratio (washing, stripping), filling rate of the steam cracking tank, speed of advance in the steam cracking tank, rate of compression at the inlet, rate of compression at the outlet of the discharge of the reactor with the orifice diameter, supply flow rate, humidity, particle size, the measuring step consists in taking a sample of the biomass entering the steam cracking tank, and in applying a physicochemical analysis to the sample in order to characterize the sampled biomass, the measuring step consists in taking a sample of the waste gases or liquids in or at the outlet of the steam cracking tank, and in applying a physicochemical analysis to the sample in order to characterize the steam-cracked biomass, the measuring step consists in taking a sample of a specimen of steam-cracked products in or at the outlet of the steam cracking tank, and in applying a physicochemical analysis to the sample in order to characterize the steam-cracked biomass.

the measuring step consists in taking a sample of a specimen of pellets, and in applying a physicochemical analysis to the sample in order to characterize the pellets manufactured using the steam-cracked biomass, at least some of the measurement results, as well as the results of the measurement performed on a specimen of pellets obtained during the same cycle, are recorded periodically, and time-stamped, the results are injected into a blockchain, the injection is performed into a supervised learning system in order to produce the digital model, the model is determined by a series of chemical simulations.

The present disclosure also relates to a facility that implements a method of this kind.

BRIEF DESCRIPTION OF THE DRAWINGS

The present disclosure will be more clearly understood upon reading the following detailed description, which refers to the accompanying drawings and relates to a non-limiting embodiment of the invention, in which drawings:

FIG. 1 is a schematic view of a steam cracking facility.

DETAILED DESCRIPTION

Steam Cracking of Heterogeneous Biomass

The continuous or batch steam cracking method according to the present disclosure provides methods for monitoring and controlling the steam cracking conditions, making it possible to adjust the severity of the treatment (reaction time and temperature) in order to adapt to the incoming raw material and to the heterogeneity thereof over time, on the scale of years, seasons, storage time, and during the method, and of course to the qualitative variation of the incoming biomasses. It is based on the fact that the material is chemically modified by means of a thermal reaction around 200° C., preferably 205-210° C., which corresponds to the required activation energy allowing for the depolymerization and the volatilization of low-energy oxygenated compounds (in particular, the most thermolabile hemicellulose constituents) with residence times, which are also adjustable, preferably 6 to 8 minutes, and which constitute a balance between minimal reactor occupancy (economic advantage) and retained material yield (technical advantage), while increasing the calorific value of the final compound, and preserving the integrity of the other macromolecules such as the cellulose and the lignin, the latter being essential for ensuring the cohesion of the final pellet, and thus its resistance to water and to mechanical handling.

Despite this increased adaptation capacity of the method (the temperature range can also span from 180 to 220° C., the duration from 5 to 30 minutes) in order to produce a pellet having a high calorific value, it is possible, despite everything, for the steam-cracked powder to be of a level of heterogeneity that is harmful to the downstream pelletization process. It is thus necessary to have available means for managing this disparity.

In addition to the known effect of steam cracking for reducing the fibers into powder and homogenizing the biomasses, the effect of the steam treatment is measured by the density and the size grading of the product. Generally products are achieved of which the majority (>80%) is made up of particles smaller than 500 µm, and a few percent of particles remain larger than a millimeter, or indeed a few millimeters. However, for analogous conditions (essentially temperature and residence time), a variation in the product results in the presence of fractions that are much less exploded, often exhibiting preservation of long fibers or flat particles originating from the grinding before the steam cracking. The density thereof is also greater than that of the main product.

Regarding the heterogeneities of size grading following steam cracking and before pelletization, the "solid" outlet of the separation system between powder and steam (static cyclone or dynamic separator such as the PERIVAPOR® by Valmet), a screen (rotary or vibrating screen) or a densimetric table, makes it possible to easily separate the compliant powder from large particles that are insufficiently steam-cracked. The overflow is collected and then transported toward a storage means before being reintroduced into the steam cracker together with the crushed biomass.

It is thus a case of implementing, following the steam cracking, on a method for transferring powder, a granulometric or densimetric screen, which selects the much less exploded fractions, followed by a separation of the fractions and a return to the supply of the steam cracker, with the aim either of immediate retreatment, if their level of disintegration is sufficiently advanced (particles not sufficiently destructured, but already reduced in size), or of deferred treatment under steam cracking conditions more suited to their resistance, which amounts to the ability to adjust the steam cracking conditions (severity) to the biomass substrate or screen overflow.

Description of an Embodiment of a Facility

FIG. 1 is a schematic view of a facility for discontinuous steam cracking of biomass, but the general principle applies for a continuous method. The facility for steam explosion includes an evaporator (100), which generates steam, and a reactor (200), which is subjected to rapid decompression.

The facility comprises a steam cracking reactor (200) and a spark arrestor (300). The reactor (200) is filled with biomass via the valve (13). Following closure of the valve (13), the steam is introduced into the reactor via the charging valve (6). The reactor (200) is then allowed to reach the target temperature, before starting the time period at the desired temperature. Typically, approximately 20 seconds are required for reaching the desired temperature. At the end of the desired period, the valve (9) is opened to allow the explosive decompression. The steam-exploded material passes through the connection pipe and fills the collection container.

A high-pressure pump (1) supplies the steam generator (100). Heating bands (2) ensure the thermostabilization of the various items of equipment.

The facility furthermore comprises pressure gauges and sensors (3) for measuring the pressure and the temperature in the steam generator (100), as well as a pressure gauge and sensor (4) for measuring the pressure and the temperature in the reactor (200). An isolating valve (5) controls the entry of the steam into the reactor (200). A safety valve (7) limits the pressure in the steam generator (100). The reactor (200) also comprises a safety valve. The spark arrestor (300) is equipped with a pressure gauge (12). The supply of the reactor (200) is achieved by a supply chamber (14), which draws along a controlled volume of the biomass stored in a reserve (15).

The facility comprises one or more items of sampling equipment (50 to 54) for solid, liquid or gaseous specimens, for analyzing the nature of the biomass provided. These data are processed by a programmable machine (16), which controls the parameters of the facility, depending on the result of the analyses and the parameters provided by the pressure and temperature sensors. The data are furthermore stored in a memory (17), which also contains the recording of the processing model determining the parameters to apply, depending on the result of the analyses. This memory (17) is associated with a calculator, which applies supervised learning processing to the historical data stored in the memory (17), and which also controls the injection of the data into a blockchain.

Type of Biomass and Indicators

The types of biomass include:
the different species of wood, alone or mixed
the different types of agricultural residue, alone or mixed
the different types of co-products of agriculture and the agro-industry, lone or mixed
the presence or absence of barks
the presence of wood of category A, B or C, alone or mixed
a mixture of lignocellulosic materials of variable particular median sizes.

The indicators include, in isolation or in combination:
The level of heterogeneity of a mixture of biomass, by determining the variance of a physical or chemical characteristic measured over a series of samples, for example, the color, the density, the median size of the elements, the optical recognition of characteristics of the different types of biomass recorded, etc.
The nature of the biomass, in particular, by means of automatic recognition or by acquisition of information by an operator, for example, the species of wood, the maturity, the nature of the tissues (bark, core, branches, knots, stumps, etc.)

The automatic recognition can be achieved by imaging, by means of an "electronic nose," or indeed by any physicochemical measurement, which makes it possible to distinguish the types of biomass.

Severity factor and control of the facility.

The control measures for the treatment of a heterogeneous biomass take into account the optimal steam-cracking conditions, in the reactor (200).

The control measures of the parameters and of the operating point are thus selected not merely depending on the processes of destructuration of the lignocellulosic materials, but also on the typology of a steam-cracked heterogeneous biomass.

For this purpose, a digital model is developed, of control measures suitable for the type of biomass and for each combination of type of biomass, in order to have available a digital reference, which makes it possible to automatically adapt the parameters, depending on the nature of the biomass entering the reactor (200).

The construction of this model can be carried out experimentally, performing a succession of treatments of various heterogeneous biomasses, having different control measures, in order to retain the control measures corresponding to the optimization of the steam cracking of the identified biomass, depending on the quality of the pellets produced.

This model can also be drawn up by a supervised learning solution, from recorded historic data.

Finally, the model can be drawn up by simulation of chemical reactions relating to the main types of biomass, which can be supplied.

This model determines the control measures to be selected, for each class of biomass.

During a new treatment, the physicochemical analyses provide the nature and the composition of the steam-cracked biomass, and a calculator automatically determines the control measures of the facility, depending on the result of the analyses, and on the recorded digital model.

The invention claimed is:

1. A method for producing a biofuel by continuous or discontinuous steam cracking of lignocellulosic biomass, comprising:
recording a digital model of optimal steam cracking parameters depending on a typology of plant constituents of the biomass in memory of a programmable machine;
supplying a steam cracking reactor with heterogeneous biomass;
measuring the typology of the plant constituents of the biomass at least once during the steam cracking, wherein the measuring comprises taking a sample of waste gases or liquids in or at an outlet of the steam cracking tank, and applying a physicochemical analysis to the sample; and
adjusting at least one of the steam cracking parameters in a controlled manner depending on the typology of the plant constituents of the biomass and on the digital model.

2. The method of claim 1, wherein the adjusted at least one of the steam cracking parameters comprises at least one of the following parameters: severity factor, steam cracking pressure, steam cracking temperature, steam cracking duration, cessation of steam cracking, steam/solid ratio, filling rate of a steam cracking tank, speed of advance in the steam cracking tank, rate of compression at an inlet, rate of compression at an outlet of the discharge of the reactor with an orifice diameter, supply flow rate, humidity, particle size.

3. The method of claim 1, wherein the heterogenous biomass has an initial humidity of less than 27% at a time of undergoing a steam cracking treatment.

4. The method of claim 3, further comprising periodically recording and time-stamping at least some results of the measuring of the typology of the plant constituents of the biomass, as well as at least some results of measurements performed on a specimen of pellets obtained during the same steam cracking cycle.

5. The method of claim 4, further comprising injecting the results into a blockchain.

6. The method of claim 4, further comprising injecting the results into a supervised learning system for producing the digital model.

7. The method of claim 1, wherein the model is determined by a series of chemical simulations.

8. A facility producing a biofuel by steam cracking of biomass comprising a continuous or discontinuous steam cracking reactor, comprising: at least one means for taking a sample of a specimen of steam-cracked products in or at an outlet of a steam cracking tank, and a physicochemical analysis system for analyzing the sample to characterize the steam-cracked biomass, and at least one means for adjusting at least one of the following parameters: severity factor, steam cracking pressure, steam cracking temperature, steam cracking duration, cessation of steam cracking, steam/solid ratio, filling rate of the steam cracking tank, speed of advance in the steam cracking tank, rate of compression at an inlet, rate of compression at the outlet of the discharge of the reactor with the orifice diameter, supply flow rate, humidity, particle size, the adjustment means being controlled by a computer that implements a method according to claim 1.

9. A method for producing a biofuel by continuous or discontinuous steam cracking of lignocellulosic biomass, comprising:
   recording a digital model of optimal steam cracking parameters depending on a typology of plant constituents of the biomass in memory of a programmable machine;
   supplying a steam cracking reactor with heterogeneous biomass;
   measuring the typology of the plant constituents of the biomass at least once during the steam cracking; and
   adjusting at least one of the steam cracking parameters in a controlled manner depending on the typology of the plant constituents of the biomass and on the digital model;
   wherein the heterogenous biomass has an initial humidity of less than 27% at a time of undergoing a steam cracking treatment.

10. The method of claim 9, further comprising periodically recording and time-stamping at least some results of the measuring of the typology of the plant constituents of the biomass, as well as at least some results of measurements performed on a specimen of pellets obtained during the same steam cracking cycle.

11. The method of claim 10, further comprising injecting the results into a blockchain.

12. The method of claim 10, further comprising injecting the results into a supervised learning system for producing the digital model.

13. A method for producing a biofuel by continuous or discontinuous steam cracking of lignocellulosic biomass, comprising:
   recording a digital model of optimal steam cracking parameters depending on a typology of plant constituents of the biomass in memory of a programmable machine;
   supplying a steam cracking reactor with heterogeneous biomass;
   measuring the typology of the plant constituents of the biomass at least once during the steam cracking; and
   adjusting at least one of the steam cracking parameters in a controlled manner depending on the typology of the plant constituents of the biomass and on the digital model;
   wherein the measuring of the typology of the plant constituents of the biomass comprises taking a sample of a specimen of pellets, and applying a physicochemical analysis to the sample.

* * * * *